United States Patent [19]

Cantatore et al.

[11] Patent Number: 5,306,495
[45] Date of Patent: Apr. 26, 1994

[54] COMPOUNDS CONTAINING SUBSTITUTED PIPERIDINE GROUPS FOR USE AS STABILIZERS FOR ORGANIC MATERIALS

[75] Inventors: Giuseppe Cantatore, Bitonto; Graziano Vignali, Sasso Marconi, both of Italy

[73] Assignee: Ciba-Geigy Corporation, Ardsley, N.Y.

[21] Appl. No.: 846,723

[22] Filed: Mar. 2, 1992

Related U.S. Application Data

[63] Continuation of Ser. No. 719,089, Jun. 20, 1991, abandoned, which is a continuation of Ser. No. 607,213, Oct. 30, 1990, abandoned, which is a continuation of Ser. No. 389,159, Aug. 2, 1989, abandoned.

[30] Foreign Application Priority Data

Aug. 4, 1988 [IT] Italy ................... 21643A/88

[51] Int. Cl.⁵ .......................... C08K 5/3492
[52] U.S. Cl. ................... 514/100; 524/96; 524/98; 524/102; 524/103; 549/113; 549/198; 549/207; 549/212; 546/187; 546/190; 546/191
[58] Field of Search ........... 524/98, 100, 102, 103, 524/96; 546/198, 187, 190, 191; 544/113, 207, 212, 198

[56] References Cited

U.S. PATENT DOCUMENTS

| | | | |
|---|---|---|---|
| 3,904,581 | 9/1975 | Murayama et al. | 524/102 |
| 4,459,395 | 7/1984 | Cantatore | 524/100 |
| 4,504,661 | 3/1985 | Wiezer et al. | 524/100 |
| 4,525,503 | 6/1985 | Cantatore | 524/100 |
| 4,695,599 | 9/1987 | Cantatore | 524/103 |
| 4,803,234 | 2/1989 | Cantatore et al. | 524/100 |
| 4,898,688 | 2/1990 | Nakahara et al. | 524/100 |
| 4,910,238 | 3/1990 | Nakahara et al. | 524/100 |
| 4,927,925 | 5/1990 | Cantatore et al. | 524/100 |

FOREIGN PATENT DOCUMENTS 0274764 7/1988 European Pat. Off. .

OTHER PUBLICATIONS

Chemical Abstracts 110: 85286K.

New Developments in the Light Stabilization of Polypropylene, F. Henninger and F. Gugumus Pct. 1990.

*Primary Examiner*—Kriellion S. Morgan
*Attorney, Agent, or Firm*—Luther A. R. Hall

[57] ABSTRACT

Compounds containing substituted piperidine groups, of the general formula (I)

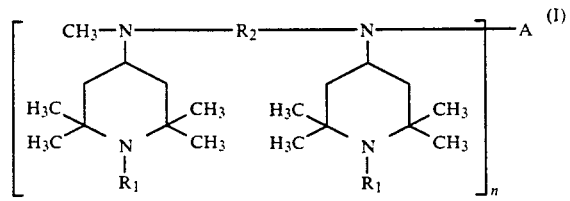

in which n is e.g. 1, 2 or 3, $R_1$ is e.g. hydrogen or methyl, $R_2$ is e.g. ethylene or trimethylene and if n is 1, A is e.g. hydrogen, $-COOC_{18}H_{37}-n$ or $-COC_{11}H_{23}-n$, if n is 2, A is e.g.

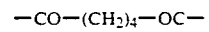

or

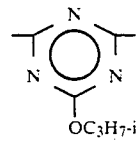

and if n is 3, A is e.g.

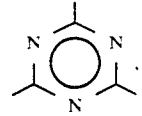

are effective stabilizers for organic materials, especially synthetic polymers, which are subject to the action of light, heat and oxidation.

12 Claims, No Drawings

COMPOUNDS CONTAINING SUBSTITUTED PIPERIDINE GROUPS FOR USE AS STABILIZERS FOR ORGANIC MATERIALS

This is a continuation of application Ser. No. 07/719,089, filed on Jun. 20, 1991, now abandoned, which is a continuation of application Ser. No. 07/607,213, filed on Oct. 30, 1990, now abandoned, which is a continuation of application Ser. No. 07/389,159, filed on Aug. 2, 1989, now abandoned.

The present invention relates to novel compounds containing substituted piperidine groups, to their use as light stabilizers, heat stabilizers and oxidation stabilizers for organic materials, particularly synthetic polymers, and to organic materials thus stabilized.

It is known that polymers undergo progressive changes in their physical properties, such as loss of mechanical strength and colour changes, when they are exposed to sunlight or other sources of ultra-violet light in the presence of oxygen. To retard the photooxidative degradation of synthetic polymers, it has been proposed to use various additives having photostabilizing properties, such as some derivatives of benzophenone and benzotriazole, nickel complexes, substituted benzoic acid esters, alkylidenemalonates, cyanoacrylates, aromatic oxamides and sterically hindered amines.

Polymeric compositions stabilized with various derivatives of diamines N,N'-disubstituted with piperidine groups have been claimed in U.S. Pat. No. 3,904,581.

In particular, the present invention relates to novel compounds of the general formula (I)

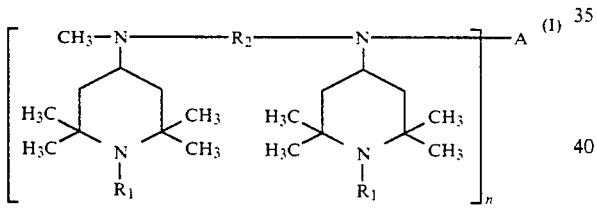

in which $R_1$ is hydrogen, $C_1$-$C_8$alkyl, O., OH, NO, $CH_2CN$, $C_1$-$C_{18}$alkoxy, $C_5$-$C_{12}$cycloalkoxy, $C_3$-$C_6$alkenyl, $C_7$-$C_9$phenylalkyl which is unsubstituted or mono-, di- or tri-substituted on the phenyl by $C_1$-$C_4$alkyl, or is $C_1$-$C_8$acyl or $C_2$-$C_4$alkyl substituted by OH in the 2-, 3- or 4-position, $R_2$ is $C_2$-$C_{12}$alkylene, and n is 1, 2, 3 or 4 and, if n is 1, A is hydrogen, $C_2$-$C_{18}$alkyl, $C_3$-$C_6$alkenyl, $C_7$-$C_9$phenylalkyl which is unsubstituted or mono-, di- or tri-substituted on the phenyl by $C_1$-$C_4$alkyl, or is $C_2$-$C_4$-alkyl substituted by OH in the 2-, 3- or 4-position, or A is one of the groups of the formula (IIa)-(IIh)

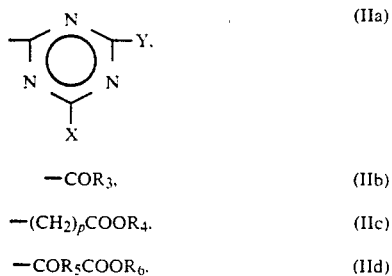

—COR$_3$, (IIb)

—(CH$_2$)$_p$COOR$_4$, (IIc)

—COR$_5$COOR$_6$, (IId)

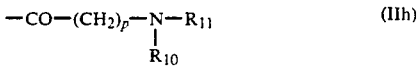

in which X and Y which can be identical or different are $C_1$-$C_{18}$alkyl, phenyl which is unsubstituted or mono-, di- or tri-substituted by $C_1$-$C_4$-alkyl, or are a group

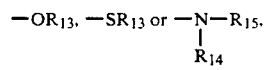

where $R_{13}$ is $C_1$-$C_{18}$alkyl, $C_5$-$C_{12}$cycloalkyl which is unsubstituted or mono-, di- or tri-substituted by $C_1$-$C_4$alkyl, or is $C_3$-$C_{18}$alkenyl, phenyl which is unsubstituted or mono-, di- or tri-substituted by $C_1$-$C_4$alkyl, or $C_7$-$C_9$phenylalkyl which is unsubstituted or mono-, di- or tri-substituted on the phenyl by $C_1$-$C_4$-alkyl, or is a group of the formula (III)

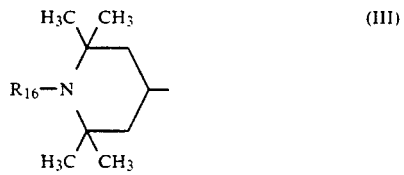

where $R_{16}$ corresponds to any of the definitions given for $R_1$, $R_{14}$ and $R_{15}$ which can be identical or different are hydrogen, $C_1$-$C_{18}$alkyl, $C_5$-$C_{12}$cycloalkyl which is unsubstituted or mono-, di- or tri-substituted by $C_1$-$C_4$alkyl, $C_7$-$C_9$phenylalkyl which is unsubstituted or mono-, di- or tri-substituted by $C_1$-$C_4$alkyl, $C_2$-$C_4$alkyl substituted in the 2-, 3- or 4-position by OH, by $C_1$-$C_8$alkoxy or by di-($C_1$-$C_4$alkyl)-amino, or are $C_3$-$C_{18}$alkenyl, tetrahydrofurfuryl or a group of the formula (III), or $R_{14}$ and $R_{15}$, together with the nitrogen atom to which they are linked, form part of a 5-membered to 7-membered heterocyclic ring, $R_3$ is hydrogen, $C_1$-$C_{18}$alkyl, $C_5$-$C_{12}$cycloalkyl which is unsubstituted or mono-, di- or tri-substituted by $C_1$-$C_4$alkyl, $C_2$-$C_{18}$alkenyl, phenyl which is unsubstituted or mono-, di- or tri-substituted by $C_1$-$C_4$alkyl and/or an OH group, $C_7$-$C_9$phenylalkyl which is unsubstituted or mono-, di- or tri-substituted on the phenyl by $C_1$-$C_4$alkyl and/or an OH group, p is zero or an integer from 1 to 5, $R_4$, $R_6$ and $R_9$ are $C_1$-$C_{18}$alkyl, $C_5$-$C_{12}$cycloalkyl which is unsubstituted or mono-, di- or tri-substituted by $C_1$-$C_4$alkyl, $C_3$-$C_{18}$alkenyl or a group of the formula (III), $R_5$ is a direct bond, $C_1$-$C_{12}$alkylene, cyclohexylene or phenylene, $R_7$ is hydrogen, $C_1$-$C_8$alkyl or phenyl, $R_8$ is ——CN or a group —COOR$_9$ with $R_9$ being as defined above, $R_{10}$ and $R_{11}$ which can be identical or different are as defined above for $R_{14}$ and $R_{15}$, and $R_{12}$ is $C_1$-$C_{18}$alkyl or phenyl which is unsubstituted or mono-, di- or tri-substituted by $C_1$-$C_4$alkyl, and, if n is 2, A is $C_2$-$C_{12}$alkylene, 2-hydroxytrimethylene, xylylene or one of the groups of the formula (IVa)-(IVe)

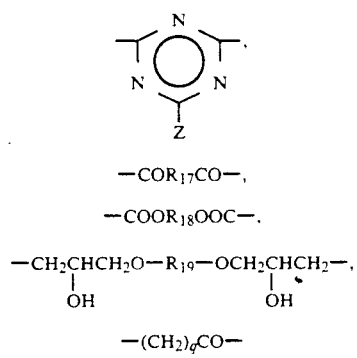
(IVa)

$$-COR_{17}CO-,\qquad(IVb)$$

$$-COOR_{18}OOC-.\qquad(IVc)$$

$$-CH_2CHCH_2O-R_{19}-OCH_2CHCH_2-,\qquad(IVd)$$
$$\phantom{-CH_2C}\underset{OH}{|}\phantom{CH_2O-R_{19}-OCH_2C}\underset{OH}{|}$$

$$-(CH_2)_qCO-\qquad(IVe)$$

in which Z is as defined above for X and Y, $R_{17}$ is as defined above for $R_5$, $R_{18}$ and $R_{19}$ are $C_2$-$C_{12}$alkylene, $C_4$-$C_{12}$alkylene which is interrupted by 1, 2 or 3 oxygen atoms, cyclohexylene, cyclohexylenedimethylene, methylenedicyclohexylene, isopropylidenedicyclohexylene, phenylene, isopropylidenediphenylene, xylylene or a group of the formula (V)

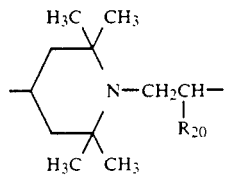
(V)

with $R_{20}$ being hydrogen, $C_1$-$C_8$alkyl or phenyl, and q is zero or an integer from 1 to 5, and, if n is 3, A is aliphatic $C_4$-$C_{18}$triacyl, aliphatic $C_6$-$C_{18}$triacyl substituted by one nitrogen atom, aromatic or heterocyclic triacyl having up to 18 carbon atoms or 1,3,5-triazine-2,4,6-triyl, and, if n is 4, A is aliphatic $C_6$-$C_{18}$tetraacyl, aliphatic $C_{10}$-$C_{18}$tetraacyl substituted by 2 nitrogen atoms, aromatic $C_{10}$-$C_{18}$tetraacyl or cycloaliphatic $C_{10}$-$C_{22}$tetraacyl.

Representative examples of $C_1$-$C_8$alkyl $R_1$, $R_7$, $R_{16}$ and $R_{20}$ are methyl, ethyl, propyl, butyl, isobutyl, pentyl, hexyl, heptyl and octyl. $C_1$-$C_4$alkyl, in particular methyl, is preferred.

Examples of alkyl having up to 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl. If A is alkyl, an alkyl group having 6 to 18 carbon atoms is preferred. Examples of OH-substituted $C_2$-$C_4$alkyl are 2-hydroxyethyl, 2-hydroxypropyl, 3-hydroxypropyl, 2-hydroxybutyl and 4-hydroxybutyl. 2-Hydroxyethyl is preferred.

Examples of $C_2$-$C_4$alkyl substituted by $C_1$-$C_8$alkoxy, preferably $C_1$-$C_4$-alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$-$C_4$alkyl substituted by di-($C_1$-$C_4$alkyl)-amino, preferably dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

Representative examples of $C_1$-$C_{18}$alkoxy $R_1$ and $R_{16}$ are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. $C_6$-$C_{12}$alkoxy, in particular heptoxy or octoxy, is preferred.

Examples of unsubstituted or substituted $C_5$-$C_{12}$cycloalkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Cyclohexyl which is unsubstituted or substituted by $C_1$-$C_4$alkyl is preferred. 4-t-Butylcyclohexyl is particularly preferred as $R_4$.

Representative examples of $C_5$-$C_{12}$cycloalkoxy $R_1$ and $R_{16}$ are cyclopentoxy, cyclohexoxy, cycloheptoxy, cyclooctoxy, cyclodecyloxy and cyclododecyloxy. Cyclopentoxy and cyclohexoxy are preferred.

Examples of alkenyl having up to 18 carbon atoms are vinyl, allyl, 2-methylallyl, hexenyl, decenyl, undecenyl and oleyl. Allyl is one of the preferred meanings of $R_1$ and $R_{16}$. If $R_1$, $R_4$, $R_6$, $R_9$-$R_{11}$, $R_{13}$-$R_{16}$ and A are alkenyl, the carbon atom in the 1-position is preferably a saturated carbon atom.

Examples of substituted phenyl are methylphenyl, dimethylphenyl, trimethylphenyl, t-butylphenyl, di-t-butylphenyl, 3,5-t-butyl-4-methylphenyl, hydroxyphenyl and 3,5-di-t-butyl-4-hydroxyphenyl.

Examples of phenylalkyl which is unsubstituted or substituted on the phenyl are benzyl, methylbenzyl, dimethylbenzyl, trimethylbenzyl, t-butylbenzyl, 2-phenylethyl and 2-(3,5-di-t-butyl-4-hydroxyphenyl)-ethyl.

Acyl $R_1$ and $R_{16}$ having up to 8 carbon atoms can be aliphatic or aromatic. Representative examples are formyl, acetyl, propionyl, butyryl, pentanoyl, hexanoyl, heptanoyl, octanoyl, benzoyl, acryloyl and crotonyl. $C_1$-$C_8$alkanoyl, $C_3$-$C_8$alkenoyl and benzoyl are preferred. Acetyl is especially preferred. If the groups

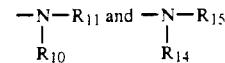

are a 5-membered to 7-membered heterocyclic group, the said heterocyclic groups preferably contain a further hetero atom, for example nitrogen or oxygen.

Representative examples are 1-pyrrolidyl, 1-piperidyl, 4-morpholinyl, 4-methyl-1-piperazinyl, 1-hexahydroazepinyl, 5,5,7-trimethyl-1-homopiperazinyl and 4,5,5,7-tetramethyl-1-homopiperazinyl.

Examples of alkylene having up to 12 carbon atoms are methylene, ethylene, propylene, trimethylene, tetramethylene, pentamethylene, 2,2-dimethyltrimethylene, hexamethylene, trimethylhexamethylene, decamethylene and dodecamethylene. $R_2$ is preferably ethylene or trimethylene.

Examples of $C_4$-$C_{12}$alkylene interrupted by 1, 2 or 3 oxygen atoms are 3-oxapentane-1,5-diyl, 3,6-dioxaoctane-1,8-diyl and 3,6,9-trioxaundecane-1,11-diyl.

Aliphatic $C_4$-$C_{18}$triacyl, preferably $C_4$-$C_{18}$alkanetrioyl, A can be unsubstituted or substituted by an OH group. Preferred examples are the triacyl derivatives of methanetricarboxylic acid, ethane-1,1,2-tricarboxylic acid, propane-1,2,3-tricarboxylic acid, citric acid or butane-1,2,3-tricarboxylic acid.

Aliphatic $C_6$-$C_{18}$triacyl A substituted by a nitrogen atom is, for example, a group N—[$(CH_2)_{1-5}CO$—$]_3$, preferably a group N—[$(CH_2)CO$—$]_3$.

Aromatic triacyl A having up to 18 carbon atoms is, for example, a triacyl derivative of benzene-1,2,4-tricarboxylic acid or benzene-1,3,5-tricarboxylic acid. acid.

Heterocyclic triacyl A having up to 18 carbon atoms is, for example,

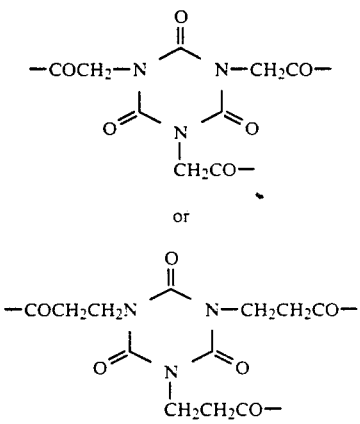

Aliphatic $C_6$-$C_{18}$tetraacyl, preferably $C_6$-$C_8$alkanetetraoyl, A is for example a tetraacyl derivative of propane-1,1,3,3-tetracarboxylic acid or butane-1,2,3,4-tetracarboxylic acid.

Aliphatic $C_{10}$-$C_{18}$tetraacyl A substituted by two nitrogen atoms is, for example, a group of the formula

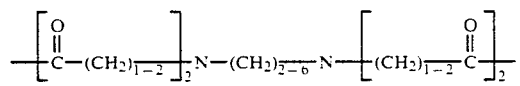

Aromatic $C_{10}$-$C_{18}$tetraacyl A is, for example, the tetraacyl derivative of benzene-1,2,4,5-tetracarboxylic acid.

Cycloaliphatic $C_{10}$-$C_{22}$tetraacyl A is, for example, one of the groups

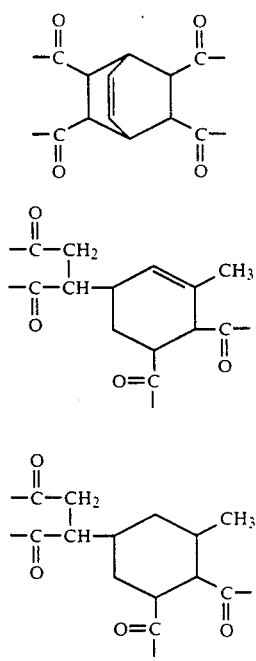

n is in particular 1, 2 or 3.

If n is 1, A is preferably a group of the formula (IIa)-(IIe). If n is 2, A is preferably a group of the formula (IVa)-(IVc). If n is 3, A is preferably 1,3,5-triazine-2,4,6-triyl.

The preferred definitions of $R_1$ are hydrogen, $C_1$-$C_4$alkyl, —OH, $C_6$-$C_{12}$alkoxy, $C_5$-$C_8$cycloalkoxy, allyl, benzyl, acetyl and 2-hydroxyethyl, in particular hydrogen and methyl.

Those compounds of the formula (I) are preferred in which $R_2$ is $C_2$-$C_{10}$alkylene, n is 1, 2, 3 or 4 and, if n is 1, A is hydrogen, $C_4$-$C_{18}$alkyl, allyl, benzyl, 2-hydroxyethyl or 2-hydroxypropyl, or A is one of the groups of the formula (IIa)-(IIh) in which X and Y which can be identical or different are $C_1$-$C_{12}$alkyl, phenyl or a group —$OR_{13}$, —$SR_{13}$ or

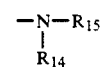

where $R_{13}$ is $C_1$-$C_{12}$alkyl, $C_5$-$C_8$cycloalky which is unsubstituted or mono-, di- or tri-substituted by $C_1$-$C_4$alkyl, $C_3$-$C_{12}$alkenyl, phenyl, benzyl or a group of the formula (III), and $R_{14}$ and $R_{15}$ which can be identical or different are hydrogen, $C_1$-$C_{18}$alkyl, $C_5$-$C_8$cycloalkyl which is unsubstituted or mono-, di- or tri-substituted by $C_1$-$C_4$alkyl, benzyl, $C_2$-$C_3$alkyl substituted in the 2-position or 3-position by OH, by $C_1$-$C_4$alkoxy or by di-($C_1$-$C_4$alkyl)-amino, allyl, oleyl, tetrahydrofurfuryl or a group of the formula (III), or the group

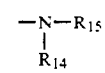

is 1-pyrrolidyl, 1-piperidyl, 4-morpholinyl or 1-hexahydroazepinyl, $R_3$ is hydrogen, $C_1$-$C_{17}$alkyl, $C_5$-$C_8$cycloalkyl which is unsubstituted or mono-, di- or tri-substituted by $C_1$-$C_4$alkyl, $C_2$-$C_{17}$alkenyl, phenyl which is unsubstituted or mono-, di- or tri-substituted by $C_1$-$C_4$alkyl and/or an OH group, $C_7$-$C_8$phenylalkyl which is unsubstituted or mono-, di- or tri-substituted on the phenyl by $C_1$-$C_4$alkyl and/or an OH group, p is zero or an integer from 1 to 3, $R_4$, $R_6$ and $R_9$ are $C_1$-$C_{18}$alkyl, $C_5$-$C_8$cycloalkyl which is unsubstituted or mono-, di- or tri-substituted by $C_1$-$C_4$alkyl, $C_3$-$C_{18}$alkenyl or a group of the formula (III), $R_5$ is a direct bond or $C_1$-$C_{10}$alkylene, $R_7$ is hydrogen or $C_1$-$C_4$alkyl, $R_8$ is —CN or a group —$COOR_9$ with $R_9$ being as defined above, $R_{10}$ and $R_{11}$ which can be identical or different are as defined above for $R_{14}$ and $R_{15}$, $R_{12}$ is $C_1$-$C_{12}$alkyl, phenyl or tolyl, and, if n is 2, A is $C_2$-$C_{10}$alkylene, 2-hydroxytrimethylene, xylylene or one of the groups of the formula (IVa)-(IVe) in which Z is as defined above for X and Y, $R_{17}$ is as defined above for $R_5$, $R_{18}$ and $R_{19}$ are $C_2$-$C_{10}$alkylene, $C_4$-$C_{10}$alkylene interrupted by 1, 2 or 3 oxygen atoms, cyclohexylenedimethylene, isopropylidenedicyclohexylene, isopropylidenediphenylene or a group of the formula (V) with $R_{20}$ being hydrogen or methyl, and q is zero or an integer from 1 to 3, and, if n is 3, A is aliphatic $C_4$-$C_8$triacyl, a group $N(CH_2CO-)_3$, a 1,3,5-triazine-2,4,6-triyl group, benzene-1,2,4-tricarbonyl, benzene-1,3,5-tricarbonyl, N,N',N''-tris(carbonylmethylene) isocyanurate or N,N',N''-tris(carbonylethylene) isocyanurate and, if n is 4, A is aliphatic $C_6$-$C_8$tetraacyl.

Those compounds of the formula (I) are particularly preferred in which $R_2$ is $C_2$-$C_8$alkylene, n is 1, 2 or 3 and, if n is 1, A is hydrogen, $C_6$-$C_{18}$-alkyl, benzyl or one of the groups of the formula (IIa)-(IIh) in which X and Y which can be identical or different are $C_1$-$C_4$alkyl, phenyl or a group —$OR_{13}$, —$SR_{13}$ or

where $R_{13}$ is $C_1$-$C_8$alkyl, cyclohexyl which is unsubstituted or mono-, di- or tri-substituted by $C_1$-$C_4$alkyl, allyl, undecenyl, phenyl, benzyl or a group of the formula (III). $R_{14}$ and $R_{15}$ which can be identical or different are hydrogen, $C_1$-$C_{16}$alkyl, cyclohexyl which is unsubstituted or mono-, di- or tri-substituted by $C_1$-$C_4$alkyl, benzyl, $C_2$-$C_3$alkyl substituted in the 2-position or 3-position by OH, by $C_1$-$C_4$alkoxy, by dimethylamino or by diethylamino, allyl, tetrahydrofurfuryl or a group of the formula (III), or the group

is 4-morpholinyl, $R_3$ is $C_1$-$C_{17}$alkyl, cyclohexyl which is unsubstituted or mono-, di- or tri-substituted by $C_1$-$C_4$alkyl, $C_2$-$C_{10}$alkenyl, phenyl, t-butylphenyl, 3,5-di-t-butyl-4-hydroxyphenyl, benzyl or 2-(3,5-di-t-butyl-4-hydroxyphenyl)ethyl, p is zero or 1, $R_4$, $R_6$ and $R_9$ are $C_1$-$C_{18}$alkyl, cyclohexyl which is unsubstituted or mono-, di- or tri-substituted by $C_1$-$C_4$alkyl, allyl, undecenyl, oleyl or a group of the formula (III). $R_5$ is a direct bond or $C_1$-$C_8$alkylene, $R_7$ is hydrogen or methyl, $R_8$ is —CN for a group —$COOR_9$ with $R_9$ being as defined above, $R_{10}$ and $R_{11}$ which can be identical or different are as defined above for $R_{14}$ and $R_{15}$, and $R_{12}$ is $C_1$-$C_8$alkyl, phenyl or tolyl, and, if n is 2, A is $C_2$-$C_8$alkylene, 2-hydroxytrimethylene, xylylene or one of the groups of the formula (IVa)-(IVe) in which Z is as defined above for X and Y, $R_{17}$ is as defined above for $R_5$, $R_{18}$ and $R_{19}$ are $C_2$-$C_8$alkylene, $C_4$-$C_8$alkylene interrupted by 1 or 2 oxygen atoms, cyclohexylenedimethylene, isopropylidenedicyclohexylene, isopropylidenediphenylene or a group of the formula (V) with $R_{20}$ being hydrogen, and q is zero or 1, and, if n is 3, A is aliphatic $C_4$-$C_8$triacyl, benzene-1,2,4-tricarbonyl, benzene-1,3,5-tricarbonyl or a 1,3,5-triazine-2,4,6-triyl group.

Those compounds of the formula (I) are of special interest in which $R_2$ is $C_2$-$C_6$alkylene, n is 1, 2 or 3 and, if n is 1, A is hydrogen or a group of the formula (IIa)-(IIe) in which X and Y which can be identical or different are $C_1$-$C_8$alkoxy or a group

where $R_{14}$ and $R_{15}$ which can be identical or different are $C_1$-$C_{12}$alkyl, cyclohexyl, benzyl, $C_2$-$C_3$alkyl substituted in the 2-position or 3-position by methoxy, by ethoxy, by dimethylamino or by diethylamino, allyl, tetrahydrofurfuryl, 2,2,6,6-tetramethyl-4-piperidyl or 1,2,2,6,6-pentamethyl-4-piperidyl, or $R_{14}$ can also be hydrogen, or the group

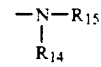

is 4-morpholinyl, $R_3$ is $C_3$-$C_{17}$alkyl, cyclohexyl, phenyl, 3,5-di-t-butyl-4-hydroxyphenyl or 2-(3,5-di-t-butyl-4-hydroxyphenyl)ethyl, p is zero, $R_4$, $R_6$ and $R_9$ are $C_2$-$C_{18}$alkyl, cyclohexyl, trimethylcyclohexyl, t-butylcyclohexyl, 2,2,6,6-tetramethyl-4-piperidyl or 1,2,2,6,6-pentamethyl-4-piperidyl, $R_5$ is a direct bond or $C_1$-$C_4$alkylene, $R_7$ is hydrogen or methyl and $R_8$ is —CN or a group —$COOR_9$ with $R_9$ being as defined above, and, if n is 2, A is one of the groups of the formula (IVa)-(IVd) in which Z is as defined above for X and Y, $R_{17}$ is a direct bond or $C_1$-$C_8$alkylene and $R_{18}$ and $R_{19}$ are $C_1$-$C_8$alkylene, cyclohexylenedimethylene, isopropylidenedicyclohexylene or isopropylidenediphenylene, and, if n is 3, A is a 1,3,5-triazine-2,4,6-triyl group.

Those compounds of the formula (I) are of particular interest in which $R_1$ is hydrogen or methyl, $R_2$ is —$(CH_2)$—$_{2-6}$, n is 1, 2 or 3 and, if n is 1, A is hydrogen or a group of the formula (IIa)-(IIe) in which X and Y which can be identical or different are $C_1$-$C_4$alkoxy or a group

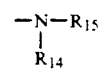

where $R_{14}$ and $R_{15}$ which can be identical or different are $C_1$-$C_{12}$alkyl, cyclohexyl, 2,2,6,6-tetramethyl-4-piperidyl or 1,2,2,6,6-pentamethyl-4-piperidyl, or $R_{14}$ can also be hydrogen, $R_3$ is $C_4$-$C_{17}$alkyl, p is zero, $R_4$, $R_6$ and $R_9$ are $C_2$-$C_{18}$alkyl, cyclohexyl or t-butylcyclohexyl, $R_5$ is a direct bond, $R_7$ is hydrogen and $R_8$ is —CN, and, if n is 2, A is one of the groups of the formula (IVa)-(IVc) in which Z is as defined above for X and Y, $R_{17}$ is $C_2$-$C_8$alkylene and $R_{18}$ is $C_4$-$C_6$alkylene, and, if n is 3, A is a 1,3,5-triazine-2,4,6-triyl group.

The compounds of the formula (I) can be prepared by processes known per se, for example by reacting a compound of the formula (VI)

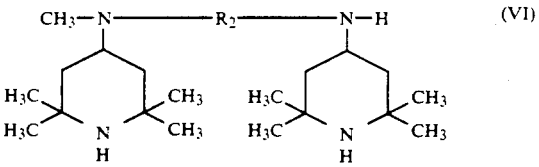

where $R_2$ is as defined above, with suitable alkylating or acylating agents in the appropriate molar ratios. This gives the compounds of the formula (I) where $R_1$=H, from which the corresponding compounds with $R_1 \neq H$ can be obtained successively.

The reactions are conveniently carried out in an inert solvent, at temperatures from e.g. −20° to 200° C., preferably from −10° to 180° C. The compounds of the formula (VI) can be prepared, for example, according to scheme 1, by reacting a compound of the formula (VII) with 2 mol of 2,2,6,6-tetramethyl-4-piperidone to give an enamine-ketimine of the formula (VIII), which is then hydrogenated in the presence of a hydrogenation catalyst such as e.g. platinum, palladium or nickel.

SCHEME 1:

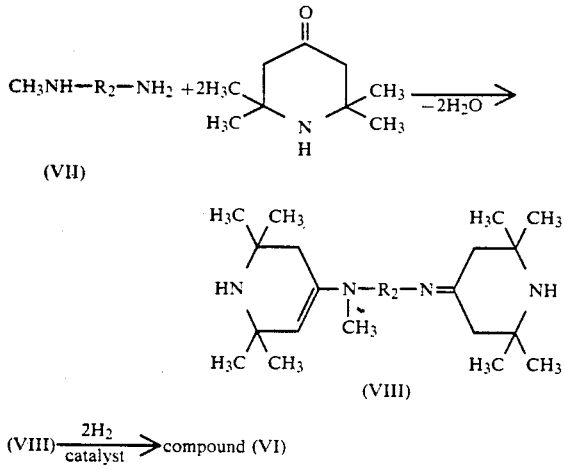

(VIII) $\xrightarrow[\text{catalyst}]{2H_2}$ compound (VI)

The reactions according to scheme 1 are preferably carried out in the same reactor without isolating the intermediate of the formula (VIII), operating without a solvent or in the presence of an aliphatic or aromatic hydrocarbon solvent having a boiling point from 60° to 180° C., preferably from 80° to 140° C.; the hydrogenation can also be carried out e.g. in the presence of a $C_1-C_4$ alcohol.

The compounds of the formula (VI) can, for example, also be prepared directly by catalytic hydrogenation of a mixture of 2,2,6,6-tetramethyl-4-piperidone and a compound of the formula (VII) in a molar ratio of 2/1, without a solvent or in a $C_1-C_4$ alcohol, preferably in the presence of an organic or inorganic acid, for example benzoic acid or sulphuric acid, in a quantity from 0.001 to 0.05 mol per mol of 2,2,6,6-tetramethyl-4-piperidone.

As mentioned at the outset, the compounds of the formula (I) are highly effective in improving the light stability, heat stability and oxidation stability of organic materials, in particular synthetic polymers and copolymers.

The invention therefore also relates to a composition containing an organic material susceptible to thermal, light-induced and oxidative degradation and at least one compound of the formula (I).

Examples of such organic materials which can be stabilized are:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high-density polyethylene (HDPE), low-denisty polyethylene (LDPE) and linear low-density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, such as, for example, ethylene/propylene, linear low-density polyethylene (LLDPE) and its mixtures with low-density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidenenorbornene; as well as mixtures of such copolymers and their mixtures with polymers mentioned in 1) above, for example polypropylene/ethylenepropylene copolymers, LDPE/EVA, LDPE/EAA, LLDPE/EVA and LLDPE/EAA.

3a. Hydrocarbon resins (for example $C_5-C_9$) and hydrogenated modifications thereof (for example tackyfiers).

4. Polystyrene, poly-(p-methylstyrene), poly-(α-methylstyrene).

5. Copolymers of styrene or α-methylstyrene with dienes or acrylic derivatives, such as, for example, styrene/acrylonitrile, styrene/alkyl methacrylate, styrene/maleic anhydride, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS, MBS, ASA or AES polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example polyvinyl chloride, polyvinylidene chloride, polyvinyl fluoride, polyvinylidene fluoride, as well as copolymers thereof, as for example vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes which are derived from polyethers, polyesters or polybutadienes with terminal hydroxyl groups on the one hand and on the other hand aliphatic or aromatic polyisocyanates, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylylenediamine and adipic acid; polyamides prepared from hexamethylenediamine and isophthalic or/and terephthalic acid and optionally an elastomer as modifier, for example poly-2,4,4-trimethylhexamethylene-terephthalamide or poly-m-phenylene-isophthalamide. Further, copolymers of the aforementioned polyamides with polyolefins, olefin copolymers, ionomers or chemically bonded or grafted elastomers; or with polyethers, such as for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly-[2,2-(4-hydroxyphenyl)-propane] terephthalate and polyhydroxybenzoates as well as block copolyetheresters derived from polyethers having hydroxyl end groups.

18. Polycarbonates and polyester-carbonates.

19. Polysulfones, polyether-sulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymer-homologous manner, such as cellulose acetates, cellulose propionates and cellulose butyrates, or cellulose ethers, such as methylcellulose; rosins and their derivatives.

27. Mixtures of polymers as mentioned above, for example PP/EPDM, polyamide 6/EPDM or ABS, PVC/EVA, PVC/ABS, PVC/MBS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubbers, for example natural latex or latexes of carboxylated styrene/butadiene copolymers.

The compounds of the formula (I) are particularly suitable for improving the light stability, heat stability and oxidation stability of polyolefins, especially polyethylene and polypropylene. The compounds of the formula (I) can be used in mixtures with organic materials in various proportions depending on the nature of the material to be stabilized, on the end use and on the presence of other additives.

In general, it is appropriate to use, for example, 0.01 to 5% by weight of the compounds of the formula (I), relative to the weight of the material to be stabilized, preferably from 0.05 to 1%.

The compounds of the formula (I) can be incorporated in the polymeric materials by various processes, such as e.g. dry mixing in the form of powder, or wet mixing in the form of solutions or suspensions or also in the form of a masterbatch; in such operations, the polymer can be used in the form of powder, granules, solutions, suspensions or in the form of latices.

The materials stabilized with the products of the formula (I) can be used for the production of e.g. mouldings, films, tapes, monofilaments, surface coatings and the like.

If desired, other conventional additives for synthetic polymers, such as e.g. antioxidants, UV absorbers, nickel stabilizers, pigments, fillers, plasticizers, antistatic agents, flameproofing agents, lubricants, corrosion inhibitors and metal deactivators, can be added to the mixtures of the compounds of the formula (I) with the organic materials.

Particular examples of additives which can be used in a mixture with the compounds of the formula (I) are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n- butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl] terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4hydroxybenzyl) sulfide, isooctyl 3,5-di-tert butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, di-octadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl) isocyanurate.

1.6. Acylaminophenols, for example lauric acid 4-hydroxyanilide, stearic acid 4-hydroxyanilide, 2,4-bis-(octylmercapto)-6-(3,5-di-tert-butyl-4-hydroxyanilino)-s-triazine, octyl N-(3,5-di-tert-butyl-4-hydroxyphenyl)-carbamate.

1.7. Esters of β-(3,5-di-tert-butyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.9. Esters of β-(3,5-dicyclohexyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.10. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)-trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy,3',5'-di-tert-amyl and 3',5'-bis(α, α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl, 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β, β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2.2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6-pentamethylpiperidyl) sebacate, bis-(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl) 1,2,3,4-butanetetracarboxylate, 1,1'-(1,2-ethanediyl)bis(3,3,5,5-tetramethylpiperazinone).

2.7. Oxalic acid diamides, for example 4,4'-dioctyloxyoxanilide, 2,2'-dioctyloxy-5,5'-di-tert-butyloxanilide, 2,2'-didodecyloxy-5,5'-di-tertbutyloxanilide, 2-ethoxy-2'-ethyloxanilide, N,N'-bis(3-dimethylaminopropyl)oxalamide, 2-ethoxy-5-tert-butyl-2'-ethyloxanilide and its mixtures with 2-ethoxy-2'-ethyl-5,4'-di-tert-butyoxanilide and mixtures of ortho- and paramethoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalodihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl) 4,4'-biphenylenediphosphonite, 3,9-bis(2,4-di-tertbutylphenoxy)-2,4,8,10-tetraoxa-3,9-diphosphaspiro[5.5] undecane.

5. Peroxide scavengers, for exmample esters of $\beta$-thiodipropionic acid, for example the lauryl, stearyl, myristyl or tridecyl sesters, mercaptobenzimidazole or the zinc salt of 2-mercaptobenzimidazole, zinc dibutyldithiocarbamate, dioctadecyl disulfide, pentaerythritol tetrackis($\beta$-dodecylmercapto)propionate.

6. Polyamide stabilisers, for example copper salts in combination with iodides and/or phosphorus compounds and salts of divalent manganese.

7. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example Ca stearate, Zn stearate, Mg stearate, Na ricinoleate and K palmitate, antimony pyrocatecholate or zinc pyrocatecholate.

8. Nucleating agents, for example 4-tert-butyl-benzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxides, carbon black, graphite.

10. Other additives, for example plasticisers, lubricants, emulsifiers, pigments, optical brighteners, flameproofing agents, antistatic agents and blowing agents.

In order to illustrate the present invention more clearly, several examples of the preparation of compounds of the formula (I) are described below; these examples are given by way of illustration only and do not imply any restriction. Particularly preferred compounds of formula (I) are those described in Examples 1, 5, 8, 10, 13 and 18.

EXAMPLE 1

Preparation of N-methyl-N,N'-bis(2,2,6,6-tetramethyl-4-piperidyl)-1,3-propanediamine 155.2 g (1 mol) of 2,2,6,6-tetramethyl-4-piperidone, 44.1 g (0.5 mol) of N-methyl-1,3-propanediamine and 250 ml of toluene are heated under reflux with elimination of the water of reaction.

The solvent is removed in vacuo and the resulting oily residue is diluted with 250 ml of methanol and hydrogenated at 80° C. in the presence of 2 g of 5% Pt on carbon under a hydrogen pressure of 50 bar until absorption is complete (about 8 hours).

After cooling to ambient temperature, the catalyst is removed by filtration and the product is separated off by distillation; boiling point 142° C./0.133 mbar.

Analysis for $C_{22}H_{46}N_4$ calculated: C=72.07%; H=12.65%; N=15.28%. found: C=71.95%; H=12.59%; N=15.30%.

EXAMPLE 2

Preparation of N-methyl-N,N'-bis(2,2,6,6-tetramethyl-4-piperidyl)-1,2-ethanediamine N-Methyl-N,N'-bis(2,2,6,6-tetramethyl-4-piperidyl)-1,2-ethanediamine is prepared as described in Example 1, using N-methyl-1,2-ethanediamine in place of N-methyl-1,3-propanediamine.

Boiling point 166° C./1.33 mbar.

Analysis for $C_{21}H_{44}N_4$ calculated: C=71.53%; H=12.58%; N=15.89%. found: C=71.06%; H=12.52%; N=15.80%.

EXAMPLE 3

Preparation of the compound

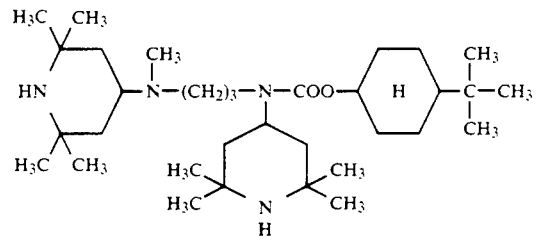

A solution of 14.4 g (0.066 mol) of 4-t-butylcyclohexyl chloroformate in 30 ml of dichloromethane is added slowly to a solution, cooled to −5° C., of 21.9 g (0.06 mol) of N-methyl-N,N'-bis(2,2,6,6-tetramethyl-4-piperidyl)-1,3-propanediamine in 100 ml of dichloromethane.

The temperature is maintained at about 0° C. during the addition.

The solution is stirred for 2 hours at 10°-15° C. and then cooled to 0° C.

A solution of 2.8 g (0.07 mol) of sodium hydroxide in 15 ml of water is added slowly while maintaining the temperature at 0°-5° C.

After one hour at this temperature, the organic phase is separated off, washed with water, dried over $Na_2SO_4$ and evaporated.

The residue is crystallized from acetonitrile, a product of melting point 95°-97° C. being obtained.

Analysis for $C_{33}H_{64}N_4O_2$ calculated: C=72.21%; N=11.75%; N=10.21%. found: C=71.93%; H=11.76%; N=10.14%.

EXAMPLES 4-10

Following the procedure described in Example 3 and using the appropriate reagents, the following compounds of the formula are prepared:

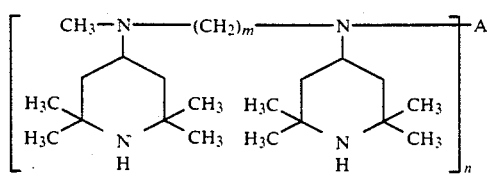

taken up in 100 ml of acetone, filtered and evaporated in vacuo. This gives the product as an oil.

Analysis for $C_{28}H_{51}N_5O_2$ calculated: C=68.67%; H=10.50%; N=14.30%. found: C=68.24%; H=10.48%; N=14.20%.

EXAMPLE 12

Preparation of the compound

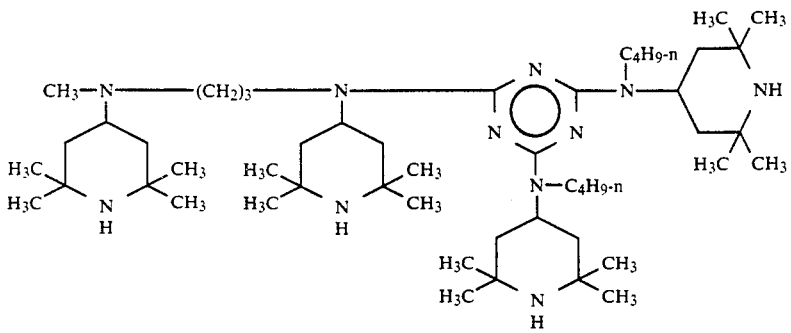

| Example | n | m | A | m.p. (°C.) |
|---|---|---|---|---|
| 4 | 1 | 2 | —CO—C(CH₃)₃ | 106-108 |
| 5 | 1 | 3 | —COOC₁₈H₃₇-n | oil |
| 6 | 1 | 3 | —COCOOC₂H₅ | 78-79 |
| 7 | 1 | 3 | —CO—C(CH₃)₃ | 96-97 |
| 8 | 1 | 3 | —CO—C₁₁H₂₃-n | 66-69 |
| 9 | 2 | 3 | —COO(CH₂)₄OOC— | 108-109 |
| 10 | 2 | 3 | —CO(CH₂)₄OC— | 106-107 |

EXAMPLE 11

64.3 g (0.12 mol) of 2-chloro-4,6-bis[N-(2,2,6,6-tetramethyl-4-piperidyl)butylamino]-1,3,5-triazine, 43.9 g (0.12 mol) of N-methyl-N,N'-bis(2,2,6,6-tetramethyl-4-piperidyl)-1,3-propanediamine and 7.2 g (0.18 mol) of sodium hydroxide in 180 ml of mesitylene are heated under reflux for 18 hours with azeotropic elimination of the water of reaction.

The mixture is cooled to about 50° C. and filtered, and the filtrate is washed with water. The solution is then dried over sodium sulphate and evaporated in vacuo (2 mbar).

The residue is taken up in n-hexane, from which the product of melting point 146°-148° C. crystallizes.

Analysis for $C_{51}H_{99}N_{11}$: calculated: C=70.70%; H=11.52%; N=17.78%. found: C=70.71%; H=11.54%; N=17.76.

EXAMPLE 13

Preparation of the compound

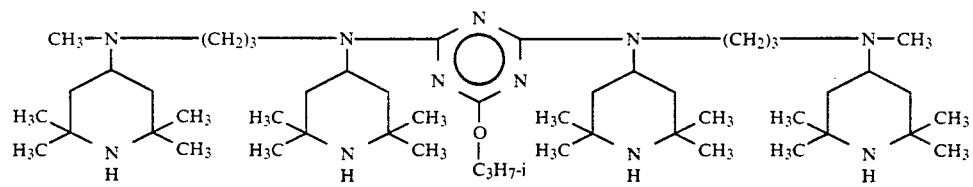

Preparation of the compound

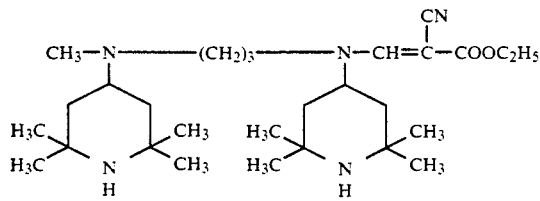

16.9 g (0.1 mol) of ethyl 2-cyano-3-ethoxyacrylate are added to a solution of 36.6 g (0.1 mol) of N-methyl-N,N'-bis(2,2,6,6-tetramethyl-4-piperidyl)-1,3-propanediamine in 80 ml of ethanol.

The solution is stirred at room temperature for 24 hours and evaporated in vacuo; the resulting residue is 12.5 g (0.06 mol) of 2,4-dichloro-6-isopropoxy-1,3,5-triazine, 43.6 g (0.12 mol) of N-methyl-N,N'-bis(2,2,6,6-tetramethyl-4-piperidyl)-1,3-propanediamine and 100 ml of mesitylene are heated for 2 hours at 90° C. 6 g (0.15 mol) of sodium hydroxide are added, and the mixture is heated under reflux for 18 hours with elimination of the water of reaction.

The mixture is cooled to about 50° C., filtered and evaporated in vacuo (2 mbar).

The product has a melting point of 50°-53° C.

Analysis for $C_{50}H_{97}N_{11}O$ calculated: C=69.16%; H=11.26%; N=17.65%. found: C=68.63%; H=11.21%; N=17.65%.

EXAMPLES 14-17

Following the procedure described in Example 13 and using the appropriate reagents, the following compounds of the formula

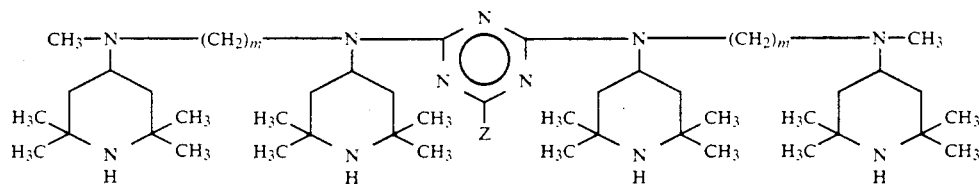

are prepared:

| Example | m | Z | m.p. (°C.) |
|---|---|---|---|
| 14 | 2 | —N(C$_2$H$_5$)$_2$ | 67-68 |
| 15 | 2 | —NH—C(CH$_3$)$_2$—CH$_2$—C(CH$_3$)$_2$—CH$_3$ | 74-75 |
| 16 | 3 | —NH—cyclohexyl | 136-138 |
| 17 | 3 | —NH—C$_{12}$H$_{25}$-n | resin |

EXAMPLE 18

Preparation of the compound

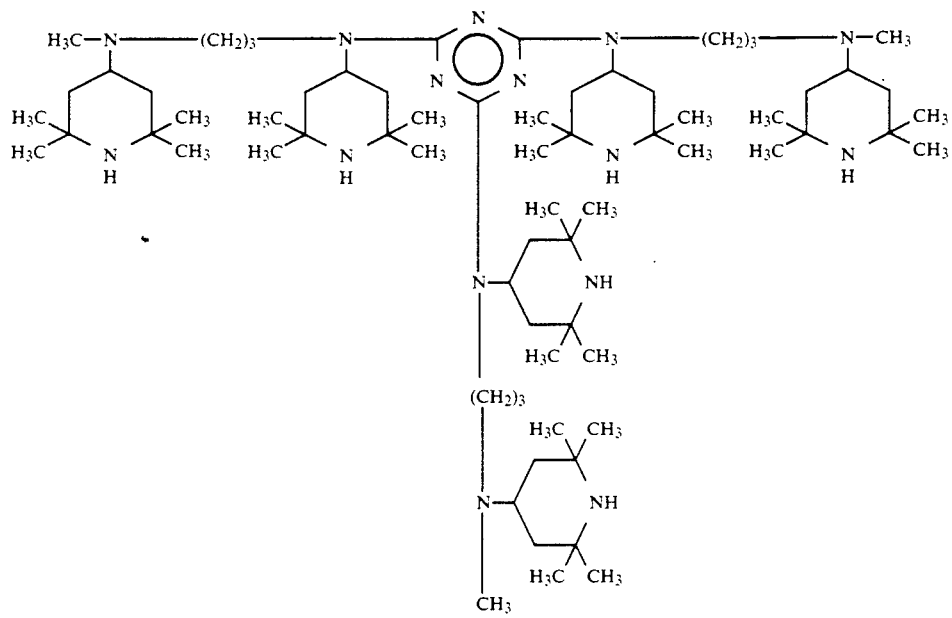

A solution of 9.2 g (0.05 mol) of cyanuric chloride in 50 ml of mesitylene is added slowly to a solution of 54.9 g (0.15 mol) of N-methyl-N,N'-bis(2,2,6,6-tetramethyl-4-piperidyl)-1,3-propanediamine in 140 ml of mesitylene.

The mixture is heated for 4 hours at 60° C., 27.6 g (0.2 mol) of potassium carbonate are added and heating is then continued under reflux for 18 hours with removal of the water of reaction.

The mixture is then cooled to about 50° C., filtered and evaporated in vacuo (2 mbar). The product has a melting point of 63°-65° C.

Analysis for C$_{69}$H$_{135}$N$_{15}$: calculated: C=70.54%; H=11.58%; N=17.88%. found: C=69.91%; H=11.50%; N=17.78%.

EXAMPLE 19

Preparation of the compound

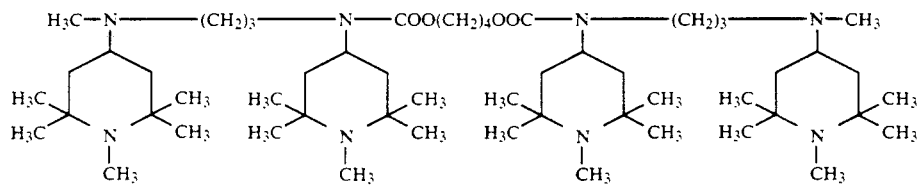

A mixture of 43.7 g (0.05 mol) of the compound from Example 9, 9 g (0.3 mol) of paraformaldehyde and 200 ml of xylene is hydrogenated at a temperature of 100° C. and under a pressure of 20 bar in the presence of a suspension of 1 g of 5% Pd on carbon in 70 ml of water.

After the catalyst has been separated off by filtration, the organic phase is washed with water, dried over $Na_2SO_4$ and evaporated in vacuo (2 mbar).

This gives the product as a heavy oil.

Analysis for $C_{54}H_{106}N_8O_4$ calculated: C=69.63%; H=11.47%; N=12.03%. found: C=69.70%; H=11.47%; N=12.02%.

EXAMPLES 20-21

Following the procedure described in Example 19 and using the appropriate reagents, the following compounds of the formula

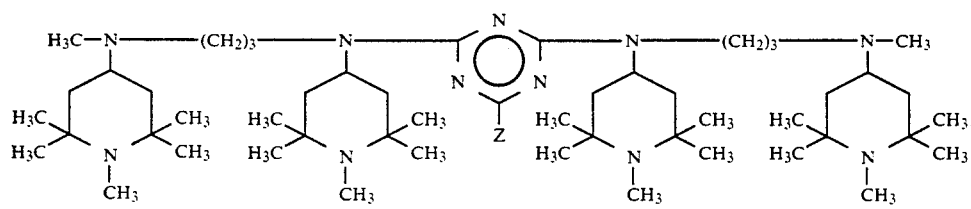

are prepared:

| Example | Z | m.p. (°C.) |
|---------|---|-----------|
| 20 | —NH—⟨C₆H₁₁⟩ | 75-78 |
| 21 | —NH—$C_{12}H_{25}$-n | 55-60 |

EXAMPLE 22

Light-stabilizing action in polypropylene tapes. 1 g of each of the compounds indicated in Table 1, 0.5 g of tris-(2,4-di-t-butylphenyl) phosphite, 0.5 g of pentaerythritol tetrakis[3-(3,5-di-t-butyl-4-hydroxyphenyl)-propionate] and 1 g of calcium stearate are mixed in a slow mixer with 1,000 g of polypropylene powder of melt index=2 g/10 min (measured at 230° C. and 2.16 kg).

The mixtures are extruded at 200°-220° C. to give polymer granules which are then converted into stretched tapes of 50 μm thickness and 2.5 mm width, using a pilot-type apparatus (Leonard-Sumirago (VA) Italy) and operating under the following conditions:
extruder temperature: 210°-230° C.
head temperature: 240°-260° C.
stretch ratio: 1:6.

The tapes thus prepared are exposed, mounted on white card, in a 65 WR weather-O-meter (ASTM G26-77) at a black panel temperature of 63° C.

The residual tenacity is measured on samples, taken after various times of exposure to light, by means of a constant-speed tensometer; the exposure time (in hours) needed to halve the initial tenacity is then calculated ($T_{50}$).

Tapes prepared under the same conditions as indicated above, but without the addition of stabilizer, are exposed for comparison.

The results obtained are shown in Table 1.

TABLE 1

| Stabilizer | $T_{50}$ (hours) |
|---|---|
| without stabilizer | 500 |
| compound from Example 6 | 2540 |
| compound from Example 7 | 2180 |
| compound from Example 8 | 2660 |
| compound from Example 9 | 2760 |
| compound from Example 10 | 2960 |
| compound from Example 11 | 2180 |
| compound from Example 13 | 3010 |
| compound from Example 16 | 2000 |
| compound from Example 18 | 2890 |
| compound from Example 20 | 2880 |
| compound from Example 21 | 2860 |

EXAMPLE 23

Light-stabilizing action in polypropylene plaques, 1 g of each of the compounds indicated in Table 2, 0.5 g of tris-(2,4-di-t-butylphenyl) phosphite, 0.5 g of pentaerythritol tetrakis[3-(3,5-di-t-butyl-4-hydroxyphenyl)-propionate], 1 g of phthalocyanine blue, 1 g of calcium stearate and 1,000 g of polypropylene powder of melt index=2.1 g/10 min (measured at 230° C. and 2.16 kg) are intimately mixed in a slow mixer.

The resulting mixtures are extruded at a temperature of 200°-220° C. to give polymer granules which are then converted into plaques of 2 mm thickness by compression-moulding at 190°-220° C.

The plaques obtained are exposed in a 65 WR model weather-O-meter (ASTM G 26-77) at a black panel temperature of 63° C. until surface embrittlement (chalking) starts.

A polypropylene plaque prepared under the same conditions as indicated above, but without the addition of compounds of the invention, is exposed for comparison.

The exposure time (in hours) required for the onset of surface embrittlement is shown in Table 2.

TABLE 2

| Stabilizer | Embrittlement time (hours) |
|---|---|
| without stabilizer | 550 |
| compound from Example 3 | 4000 |
| compound from Example 5 | 4250 |
| compound from Example 6 | 3550 |
| compound from Example 7 | 3760 |
| compound from Example 8 | 4400 |
| compound from Example 9 | 4000 |
| compound from Example 10 | 3520 |
| compound from Example 11 | 3550 |

What is claimed is:
1. A compound of formula I

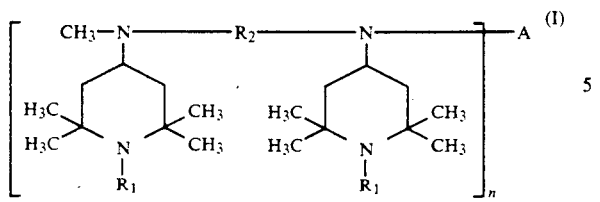

in which $R_1$ is hydrogen, $C_1-C_8$alkyl, O., OH, NO, $CH_2CN$, $C_1-C_{18}$alkoxy, $C_5-C_{12}$ cycloalkoxy, $C_3-C_6$alkenyl, $C_7-C_9$phenylalkyl which is substituted or mono-, di- or tri-substituted on the phenyl by $C_1-C_4$alkyl, or is $C_1-C_8$acyl or $C_2-C_4$alkyl substituted by OH in the 2-, 3- or 4-position, $R_2$ is $C_2-C_{12}$alkylene, n is 1, 2, 3 or 4 and, if n is 1, A is $C_2-C_{18}$alkyl, $C_3-C_6$alkenyl, $C_7-C_9$phenylalkyl which is unsubstituted or mono-, di- or tri-substituted on the phenyl by $C_1-C_4$alkyl, or is $C_2-C_4$-alkyl substituted by OH in the 2-, 3- or 4-position, or A is one of the groups of the formula (IIa)–(IIb) or (IId)–(IIh)

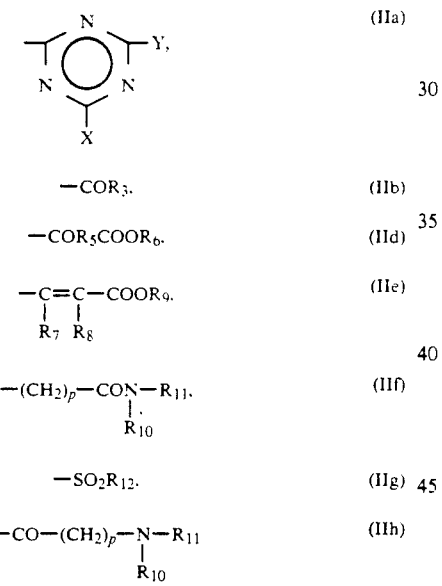

$$-COR_3. \qquad (IIb)$$

$$-COR_5COOR_6. \qquad (IId)$$

$$\underset{R_7 \ R_8}{-C=C-COOR_9}. \qquad (IIe)$$

$$-(CH_2)_p-\underset{\underset{R_{10}}{|}}{CON}-R_{11}. \qquad (IIf)$$

$$-SO_2R_{12}. \qquad (IIg)$$

$$-CO-(CH_2)_p-\underset{\underset{R_{10}}{|}}{N}-R_{11} \qquad (IIh)$$

in which X and Y which can be identical or different are $C_1-C_{18}$alkyl, phenyl which is unsubstituted or mono-, di- or tri-substituted by $C_1-C_4$-alkyl, or are a group $-OR_{13}$, $-SR_{13}$ or

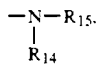

where $R_{13}$ is $C_1-C_{18}$alkyl, $C_5-C_{12}$cycloalkyl which is unsubstituted or mono-, di- or tri-substituted by $C_1-C_4$alkyl, or is $C_3-C_{18}$alkenyl, phenyl which is unsubstituted or mono-, di- or tri-substituted by $C_1-C_4$alkyl, or $C_7-C_9$phenylalkyl which is unsubstituted or mono-, di- or tri-substituted on the phenyl by $C_1-C_4$alkyl, or is a group of the formula (III)

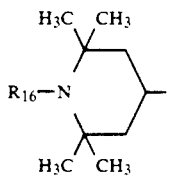

where $R_{16}$ corresponds to any of the definitions given for $R_1$, $R_{14}$ and $R_{15}$ which can be identical or different are hydrogen, $C_1-C_{18}$alkyl, $C_5-C_{12}$-cycloalkyl which is unsubstituted or mono-, di- or tri-substituted by $C_1-C_4$alkyl, $C_7-C_9$phenylalkyl which is unsubstituted or mono-, di- or tri-substituted by $C_1-C_4$alkyl, $C_2-C_4$alkyl substituted in the 2-, 3- or 4-position by OH, by $C_1-C_8$alkoxy or by di-($C_1-C_4$alkyl)-amino, or are $C_3-C_{18}$-alkenyl, tetrahydrofurfuryl or a group of the formula (III), or $R_{14}$ and $R_{15}$, together with the nitrogen atom to which they are linked, form part of a 5-membered to 7-membered heterocyclic ring which is 1-pyrrolidyl, 1-piperidyl, 4-morpholinyl, 4-methyl-1-piperazinyl, 1-hexahydroazepinyl, 5,5,7-trimethyl-1-homopiperazinyl or 4,5,5,7-tetramethyl-1-homopiperazinyl, $R_3$ is hydrogen, $C_1-C_{18}$-alkyl, $C_5-C_{12}$cycloalkyl which is unsubstituted or mono-, di-or tri-substituted by $C_1-C_4$alkyl, $C_2-C_{18}$alkenyl, phenyl which is unsubstituted or mono-, di- or tri-substituted by $C_1-C_4$alkyl and/or an OH group, $C_7-C_9$-phenylalkyl which is unsubstituted or mono-, di- or tri-substituted on the phenyl by $C_1-C_4$alkyl and/or an OH group, p is zero or an integer from 1 to 5, $R_6$ and $R_9$ are $C_1-C_{13}$alkyl, $C_5-C_{12}$cycloalkyl which is unsubstituted or mono-, di- or tri-substituted by $C_1-C_4$alkyl, $C_3-C_{18}$-alkenyl or a group of the formula (III), $R_5$ is a direct bond, $C_1-C_{12}$-alkylene, cyclohexylene or phenylene, $R_7$ is hydrogen, $C_1-C_8$alkyl or phenyl $R_8$ is $-CN$ or a group $-COOR_9$ with $R_9$ being as defined above, $R_{10}$ and $R_{11}$ which can be identical or different are as defined above for $R_{14}$ and $R_{15}$, and $R_{12}$ is $C_1-C_{18}$alkyl or phenyl which is unsubstituted or mono-, di- or tri-substituted by $C_1-C_4$alkyl, and, if n is 2, A is $C_2-C_{12}$alkylene, 2-hydroxytrimethylene, xylylene or one of the groups of the formula (IVa)–(IVe)

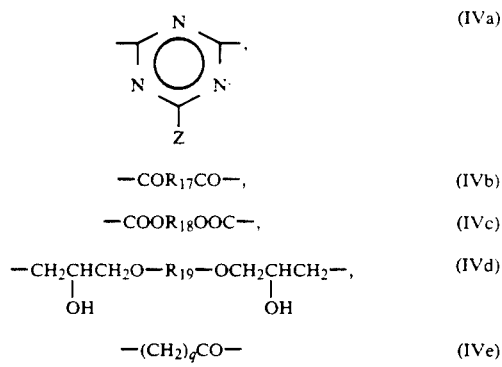

$$-COR_{17}CO-, \qquad (IVb)$$

$$-COOR_{18}OOC-, \qquad (IVc)$$

$$-CH_2\underset{OH}{\overset{|}{CH}}CH_2O-R_{19}-OCH_2\underset{OH}{\overset{|}{CH}}CH_2-, \qquad (IVd)$$

$$-(CH_2)_qCO- \qquad (IVe)$$

in which Z is as defined above for X and Y, $R_{17}$ is as defined above for $R_5$, $R_{18}$ and $R_{19}$ are $C_2-C_{12}$alkylene, $C_4-C_{12}$alkylene which is interrupted by 1, 2 or 3 oxygen atoms, cyclohexylene, cyclohexylenedimethylene, methylenedicyclohexylene, isopropylidenedicyclohexylene, phenylene, isopropylidenediphenylene, xylylene or a group of the formula (V)

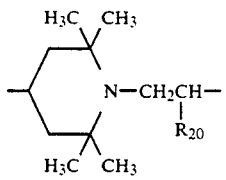

with $R_{20}$ being hydrogen, $C_1$-$C_8$alkyl or phenyl, and q is zero or an integer from 1 to 5, and, if n is 3, A is aliphatic $C_4$-$C_{18}$triacyl, aliphatic $C_6$-$C_{18}$triacyl substituted by one nitrogen atom, aromatic or heterocyclic triacyl having up to 18 carbon atoms or 1,3,5-triazine-2,4,6-triyl, and, if n is 4, A is aliphatic $C_6$-$C_{18}$tetraacyl, aliphatic $C_{10}$-$C_{18}$tetraacyl substituted by two nitrogen atoms, aromatic $C_{10}$-$C_{18}$tetraacyl or cycloaliphatic $C_{10}$-$C_{22}$tetraacyl.

2. A compound of the formula (I) according to claim 1, wherein $R_1$ is hydrogen, $C_1$-$C_4$alkyl, OH, $C_6$-$C_{12}$alkoxy, $C_5$-$C_8$cycloalkoxy, allyl, benzyl, acetyl or 2-hydroxyethyl.

3. A compound of the formula (I) according to claim 1, wherein $R_2$ is $C_2$-$C_{10}$alkylene, n is 1, 2, 3 or 4 and, if n is 1, A is $C_4$-$C_{18}$alkyl, allyl, benzyl, 2-hydroxyethyl or 2-hydroxypropyl, or A is one of the groups of the formula (IIa)-(IIb) or (IId)-(IIh) in which X and Y which can be identical or different are $C_1$-$C_{12}$alkyl, phenyl or a group —$OR_{13}$, —$SR_{13}$ or

where $R_{13}$ is $C_1$-$C_{12}$alkyl, $C_5$-$C_8$cycloalkyl which is unsubstituted or mono-, di- or tri-substituted by $C_1$-$C_4$alkyl, $C_3$-$C_{12}$alkenyl, phenyl, benzyl or a group of the formula (III), and $R_{14}$ and $R_{15}$ which can be identical or different are hydrogen, $C_1$-$C_{18}$alkyl, $C_5$-$C_8$cycloalkyl which is unsubstituted or mono-, di- or tri-substituted by $C_1$-$C_4$alkyl, benzyl, $C_2$-$C_3$alkyl substituted in the 2-position or 3-position by OH, by $C_1$-$C_4$alkoxy or by di-($C_1$-$C_4$alkyl)-amino, allyl, oleyl, tetrahydrofurfuryl or a group of the formula (III), or the group

is 1-pyrrolidyl, 1-piperidyl, 4-morpholinyl or 1-hexahydroazepinyl, $R_3$ is hydrogen, $C_1$-$C_{17}$alkyl, $C_5$-$C_8$cycloalkyl which is unsubstituted or mono-, di- or tri-substituted by $C_1$-$C_4$alkyl, $C_2$-$C_{17}$alkenyl, phenyl which is unsubstituted or mono-, di- or tri-substituted by $C_1$-$C_4$alkyl and/or an OH group, $C_7$-$C_8$phenylalkyl which is unsubstituted or mono-, di- or tri-substituted on the phenyl by $C_1$-$C_4$alkyl and/or an OH group, p is zero or an integer from 1 to 3, $R_6$ and $R_9$ are $C_1$-$C_{18}$alkyl, $C_5$-$C_8$cycloalkyl which is unsubstituted or mono-, di- or tri-substituted by $C_1$-$C_4$alkyl, $C_3$-$C_{18}$alkenyl or a group of the formula (III), $R_5$ is a direct bond or $C_1$-$C_{10}$alkylene, $R_7$ is hydrogen or $C_1$-$C_4$alkyl, $R_8$ is —CN or a group —$COOR_9$ with $R_9$ being as defined above, $R_{10}$ and $R_{11}$ which can be identical or different are as defined above for $R_{14}$ and $R_{15}$, $R_{12}$ is $C_1$-$C_{12}$alkyl, phenyl or tolyl, and, if n is 2, A is $C_2$-$C_{10}$alkylene, 2-hydroxytrimethylene, xylylene or one of the groups of the formula (IVa)-(IVe) in which Z is as defined above for X and Y, $R_{17}$ is as defined above for $R_5$, $R_{18}$ and $R_{19}$ are $C_2$-$C_{10}$alkylene, $C_4$-$C_{10}$alkylene interrupted by 1, 2 or 3 oxygen atoms, cyclohexylenedimethylene, isopropylidenedicyclohexylene, isopropylidenediphenylene or a group of the formula (V) with $R_{20}$ being hydrogen or methyl, and q is zero or an integer from 1 to 3, and, if n is 3, A is aliphatic $C_4$-$C_8$triacyl, a group N—$(CH_2CO—)_3$, a 1,3,5-triazine-2,4,6-triyl group, benzene-1,2,4-tricarbonyl, benzene-1,3,5-tricarbonyl, N,N',N''-tris-(carbonylmethylene) isocyanurate or N,N',N''-tris-(carbonylethylene) isocyanurate and, if n is 4, A is aliphatic $C_6$-$C_8$tetraacyl.

4. A compound of the formula (I) according to claim 1, wherein $R_2$ is $C_2$-$C_8$alkylene, n is 1, 2 or 3 and, if n is 1, A is $C_6$-$C_{18}$-alkyl, benzyl or one of the groups of the formula (IIa)-(IIb) or (IId)-(IIh) in which X and Y which can be identical or different are $C_1$-$C_4$alkyl, phenyl or a group —$OR_{13}$, —$SR_{13}$ or

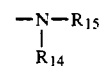

where $R_{13}$ is $C_1$-$C_8$alkyl, cyclohexyl which is unsubstituted or mono-, di- or tri-substituted by $C_1$-$C_4$alkyl, allyl, undecenyl, phenyl, benzyl or a group of the formula (III), $R_{14}$ and $R_{15}$ which can be identical or different are hydrogen, $C_1$-$C_{16}$alkyl, cyclohexyl which is unsubstituted or mono-, di- or tri-substituted by $C_1$-$C_4$alkyl, benzyl, $C_2$-$C_3$alkyl substituted in the 2-position or 3-position by OH, by $C_1$-$C_4$alkoxy, by dimethylamino or by diethylamino, allyl, tetrahydrofurfuryl or a group of the formula (III), or the group

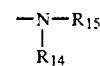

is 4-morpholinyl, $R_3$ is $C_1$-$C_{17}$alkyl, cyclohexyl which is unsubstituted or mono-, di- or tri-substituted by $C_1$-$C_4$alkyl, $C_2$-$C_{10}$alkenyl, phenyl, t-butylphenyl, 3,5-di-t-butyl-4-hydroxyphenyl, benzyl or 2-(3,5-di-t-butyl-4-hydroxyphenyl)ethyl, p is zero or 1, $R_6$ and $R_9$ are $C_1$-$C_{18}$alkyl, cyclohexyl which is unsubstituted or mono-, di- or tri-substituted by $C_1$-$C_4$alkyl, allyl, undecenyl, oleyl or a group of the formula (III), $R_5$ is a direct bond or $C_1$-$C_8$alkylene, $R_7$ is hydrogen or methyl, $R_8$ is —CN or a group —$COOR_9$ with $R_9$ being as defined above, $R_{10}$ and $R_{11}$ which can be identical or different are as defined above for $R_{14}$ and $R_{15}$, and $R_{12}$ is $C_1$-$C_8$alkyl, phenyl or tolyl, and, if n is 2, A is $C_2$-$C_8$alkylene, 2-hydroxytrimethylene, xylylene or one of the groups of the formula (IVa)-(IVe) in which Z is as defined above for X and Y, $R_{17}$ is as defined above for $R_5$, $R_{18}$ and $R_{19}$ are $C_2$-$C_8$alkylene, $C_4$-$C_8$alkylene interrupted by 1 or 2 oxygen atoms, cyclohexylenedimethylene, isopropylidenedicyclohexylene, isopropylidenediphenylene or a group of the formula (V) with $R_{20}$ being hydrogen, and q is zero or 1, and, if n is 3, A is aliphatic $C_4$-$C_8$-triacyl, benzene-1,2,4-tricarbonyl, benzene-1,3,5-tricarbonyl or a 1,3,5-triazine-2,4,6-triyl group.

5. A compound of the formula (I) according to claim 1, wherein $R_2$ is $C_2$-$C_6$alkylene, n is 1, 2 or 3 and, if n is 1, A is a group of the formula (IIa)-(IIb) or (IId)-(IIe) in which X and Y which can be identical or different are $C_1-C_8$alkoxy or a group

where $R_{14}$ and $R_{15}$ which can be identical or different are $C_1-C_{12}$alkyl, cyclohexyl, benzyl $C_2-C_3$alkyl substituted in the 2-position or 3-position by methoxy, by ethoxy, by dimethylamino or by diethylamino, allyl, tetrahydrofurfuryl, 2,2,6,6-tetramethyl-4-piperidyl or 1,2,2,6,6-pentamethyl-4-piperidyl, or $R_{14}$ can also be hydrogen, or the group

is 4-morpholinyl, $R_3$ is $C_3-C_{17}$alkyl, cyclohexyl, phenyl, 3,5-di-t-butyl-4-hydroxyphenyl or 2-(3,5-di-t-butyl-4-hydroxyphenyl)ethyl, p is zero, $R_6$ and $R_9$ are $C_2-C_{18}$alkyl, cyclohexyl, trimethylcyclohexyl, t-butylcyclohexyl, 2,2,6,6-tetramethyl-4-piperidyl or 1,2,2,6,6-pentamethyl-4-piperidyl, $R_5$ is a direct bond or $C_1-C_4$alkylene, $R_7$ is hydrogen or methyl and $R_8$ is —CN or a group —COOR$_9$ with $R_9$ being as defined above, and, if n is 2, A is one of the groups of the formula (IVa)--(IVd) in which Z is as defined above for X and Y, $R_{17}$ is a direct bond or $C_1-C_8$alkylene and $R_{18}$ and $R_{19}$ are $C_4-C_8$alkylene, cyclohexylenedimethylene, isopropylidenedicyclohexylene or isopropylidenediphenylene, and, if n is 3, A is a 1,3,5-triazine-2,4,6-triyl group.

6. A compound of the formula (I) according to claim 1, wherein $R_1$ is hydrogen or methyl, $R_2$ is —(CH$_2$)$_{2-6}$—, n is 1, 2 or 3 and if n is 1, A is a group of the formula (IIa)-(IIb) or (IId)-(IIe) in which X and Y which can be identical or different are $C_1-C_4$alkoxy or a group

where $R_{14}$ and $R_{15}$ which can be identical or different are $C_1-C_{12}$alkyl, cyclohexyl, 2,2,6,6-tetramethyl-4-piperidyl or 1,2,2,6,6-pentamethyl-4-piperidyl, or $R_{14}$ can also be hydrogen, $R_3$ is $C_4-C_{17}$alkyl, p is zero, $R_6$ and $R_9$ are $C_2-C_{18}$alkyl, cyclohexyl or t-butylcyclohexyl, $R_5$ is a direct bond, $R_7$ is hydrogen and $R_8$ is —CN, and, if n is 2, A is one of the groups of the formula (IVa)-(IVc) in which Z is as defined above for X and Y, $R_{17}$ is $C_2-C_8$alkylene and $R_{18}$ is $C_4-C_6$alkylene, and, if n is 3, A is a 1,3,5-triazine-2,4,6-triyl group.

7. A compound of the formula (I) according to claim 1, wherein $R_1$ is hydrogen, $R_2$ is —(CH$_2$)$_3$—, n is 1, 2 or 3 and if n is 1, A is —COC$_{11}$H$_{23}$—n, if n is 2, A is —CO—(CH$_2$)$_4$—CO— or

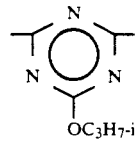

and if n is 3, A is

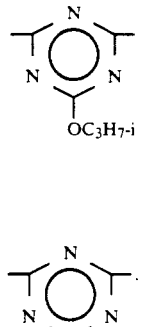

8. A composition containing a synthetic polymer susceptible to light-induced, thermal and oxidative degradation and an effective stabilizing amount of a compound of the formula (I) according to claim 1.

9. A composition according to claim 8, which, in addition to the compound of the formula (I), also contains other conventional additives for synthetic polymers.

10. A composition according to claim 8, wherein the synthetic polymer is a polyolefin.

11. A composition according to claim 8, wherein the synthetic polymer is polyethylene or polypropylene.

12. A method for stabilizing a synthetic polymer against light-induced, thermal and oxidative degradation, which comprises incorporating into said organic material an effective stabilizing amount of a compound of the formula (I) according to claim 1.

* * * * *